United States Patent [19]
Guhl

[11] Patent Number: 5,290,220
[45] Date of Patent: Mar. 1, 1994

[54] NON-INVASIVE DISTRACTION SYSTEM FOR ANKLE ARTHROSCOPY

[76] Inventor: James F. Guhl, 13455 Elmhurst Drive Pkwy., Elm Grove, Wis. 53122

[21] Appl. No.: 851,750

[22] Filed: Mar. 16, 1992

[51] Int. Cl.⁵ .............................................. A61F 5/00
[52] U.S. Cl. ...:................................ 602/33; 128/882; 602/32
[58] Field of Search ............... 128/879, 882, 898, 782; 602/5, 21, 23, 27, 32–36, 38–40; 604/164, 170; 606/53, 54, 57, 58, 86, 87, 90, 105; 5/648, 650

[56] References Cited

U.S. PATENT DOCUMENTS

| | | | |
|---|---|---|---|
| 3,020,909 | 2/1962 | Stevens | 602/39 |
| 3,135,257 | 6/1964 | Anderson | 602/39 |
| 3,745,996 | 7/1973 | Rush, Sr. | 602/39 |
| 4,350,153 | 9/1982 | Borschneck | 602/40 |
| 5,010,900 | 4/1991 | Auchinleck et al. | 128/855 |
| 5,020,525 | 6/1991 | Ewing et al. | |
| 5,025,802 | 6/1991 | Laico et al. | 128/882 |
| 5,063,918 | 11/1991 | Guhl. | |

*Primary Examiner*—Richard J. Apley
*Assistant Examiner*—Linda C. M. Dvorak
*Attorney, Agent, or Firm*—Andrus, Sceales, Starke & Sawall

[57] ABSTRACT

An apparatus and method for non-invasive distraction of the ankle joint to accommodate arthroscopic procedures provides the ability to apply a wide range of distraction forces to the ankle joint, to hold the ankle in positions above the table in leg positions ranging from nearly horizontal to acutely flexed, and to even position the ankle below the level of the operating table to accommodate special needs and/or positions. A distractor with an axially adjustable length is attached at one end to the foot of the patient and at the other end to one end of a rotatable lever arm, the opposite end of which lever arm is rotatably attached to the operating table with an adjustable clamp. With the knee of the patient supported in a conventional leg holder, the distractor is initially secured in a position extending axially away from the end of the leg by rotating the lever arm in a direction to place the distractor and ankle joint in a position of initial distraction. Further fine adjustment of the length of the distractor establishes the final desired level of distraction. The lever arm may be positioned on a hinged operating table end, thereby allowing a substantially greater variation in the height and relative position of the ankle joint.

5 Claims, 3 Drawing Sheets

NON-INVASIVE DISTRACTION SYSTEM FOR ANKLE ARTHROSCOPY

BACKGROUND OF THE INVENTION

The present invention relates to a method and apparatus for use in the performance of ankle arthroscopy procedures and, more particularly, to an improved system for providing non-invasive ankle joint distraction in support of arthroscopic procedures.

As described in my prior U.S. Pat. No. 5,063,918, it is usually necessary to provide some form of ankle joint distraction in order to create sufficient space in the joint for the arthroscope and various other surgical equipment and instruments used in ankle arthroscopy. Furthermore, the degree of distraction will vary depending on the nature of the procedure, the type and size of surgical instruments required, and the relative tightness or looseness of the joint in a particular patient. The method and apparatus in the above patent provides for the use of a basic non-invasive technique and, if the level of distraction it provides is insufficient, the ability to convert without interruption to an invasive distraction technique utilizing pinned connections between the bones of the lower leg and foot.

Relatively recent improvements in the design and construction of arthroscopic instruments include smaller size instruments requiring less space within the joint for adequate performance. In turn, the amount of ankle joint distraction may also be reduced in many cases. As a result, the importance of non-invasive distraction techniques has recently taken on somewhat greater importance relative to invasive techniques. This is also significant because the disadvantages and potential complications of invasive techniques are well documented and these techniques are only utilized when adequate distraction by non-invasive means cannot be attained.

One method of providing non-invasive ankle distraction is shown in U.S. Pat. No. 5,020,525. In this method, a removable strap is attached to the patient's foot and the opposite end of the strap is strung to an outrigger fixed to and extending several feet away from the foot of the operating table. Variable distraction force is applied in a direction generally axially of the patient's leg with a manually operated crank and pulley system. The method provides good distraction and the ability to control the amount of the distraction force. However, the horizontal position of the leg and foot results in difficult access to posterior portals of the ankle and also results in the problem of water or saline solution running down the arthroscope and into the camera. The outrigger mechanism may also create an obstacle to the surgeon. Finally, the need to convert to invasive distraction means requires complete repositioning of the patient which is cumbersome and time consuming.

In another known method, the patient is positioned supine at the end of the operating table with the hip and knee flexed and the lower leg depending downwardly from the end of the table over a padded horizontal bar behind the knee. Distraction of the ankle joint is provided by pulling vertically downward on a strap attached to the foot of the patient and secured to a pivotal cantilevered arm below the table. This method does not offer much variation in position and requires careful attention to the potential circulatory problems attendant the application of pressure to the popliteal area with the knee acutely flexed over the padded bar.

My prior U.S. Pat. No. 5,063,918 describes a non-invasive distraction technique which allows variable positioning of the ankle above the operating table to accommodate access to the ankle joint from any direction. The non-invasive methods disclosed in this patent utilize an adjustable distraction device attached between the foot of the patient and the Clark rail on the operating table to provide a variable level of joint distraction. However, two deficiencies in the method disclosed in this patent have been noted. First, the initial positioning of the distraction device by sliding it along the Clark rail and clamping it in position locates the patient's foot and ankle fairly close to the operating table, thereby somewhat inhibiting access, particularly when the leg is only slightly flexed. Second, the overall range of adjustment of the height of the ankle with respect to the top of the operating table is somewhat limited, making access inconvenient or troublesome for some surgeons and for the techniques they may wish to utilize.

SUMMARY OF THE INVENTION

In accordance with the present invention, the deficiencies in prior art non-invasive ankle distraction techniques have been overcome with a system and method which provides the ability to provide a wide range of distraction forces to the ankle joint, the ability to hold the ankle in a convenient position above the table in leg positions ranging from nearly horizontal to acutely flexed, and to position the ankle below the level of the operating table to accommodate further surgical needs and positions.

In the system of the present invention, a conventional operating table is used to support the patient on his back in a generally horizontal position. A conventional urology leg holder is used to support the patient's leg posteriorly of the knee joint where it may be maintained in a selected position between slightly flexed (nearly horizontal) and acutely flexed, with the leg holder attached directly to the operating table below the knee and including means for adjusting the height at which the knee joint is held above the table. The distraction means includes an elongate body having an axially adjustable length and a first end by which it is attached to the foot of the patient. A manually operable or rotatable lever arm has one end attached to the operating table and an opposite end attached to the second end of the body of the distractor. An adjustable clamp is attached to one edge of the operating table and includes first clamping means to fix the position of the clamp along the table edge and second clamping means to which the opposite end of the lever arm is attached, permitting the lever arm to be rotated manually in a generally vertical plane and clamped in an initial selected position to impose a tensile load on the distractor and an initial level of distraction of the ankle joint. The initial level of ankle joint distraction may be varied by adjusting means on the distractor device.

In a preferred embodiment, the operating table is provided with a hinged joint extending across the table normal to the table edge and positioned between the leg holder height adjusting means and the lever arm clamp, thereby providing a hinged table end supporting the clamp. Means are also provided for tilting the hinged table end downwardly to a variable selected acute angle position and for locking the table end in the selected position to position the clamp, lever and distraction device below the top of the table. The hinged table end supporting the second end of the distractor device may be utilized with prior art distractors not including the manually operable lever arm.

One preferred method of providing non-invasive ankle joint distraction in accordance with the present invention includes the steps of: supporting the patient on a table in a supine position; positioning the leg of the patient to selectively maintain the leg flexed above the operating table by supporting the leg beneath the knee joint; pivotally attaching one end of a lever arm to one edge of the table; attaching a first end of an axially adjustable distraction device to the foot of the patient and attaching a second end of the distraction device to the other end of the lever arm; manually rotating said one end of the lever arm about the pivotal connection in a generally vertical plane to impose a tensile load on said distraction device and provide an initial level of ankle joint distraction; clamping the other end of the lever arm to maintain said initial level of distraction; and, adjusting the length of the distraction device to vary the initial level of ankle joint distraction.

The method may also include the steps of pivoting the end of the operating table to which the lever arm is attached about a hinged joint in the table between the knee support and lever arm attachment; and locking the table end in a selected rotated position to position the lever arm and the distraction device below the top of the table. The method may also be utilized without the lever arm and with the distraction device attached directly to the edge of the table.

DETAILED DESCRIPTION OF THE PREFERRED EMBODIMENTS

Figure 1:
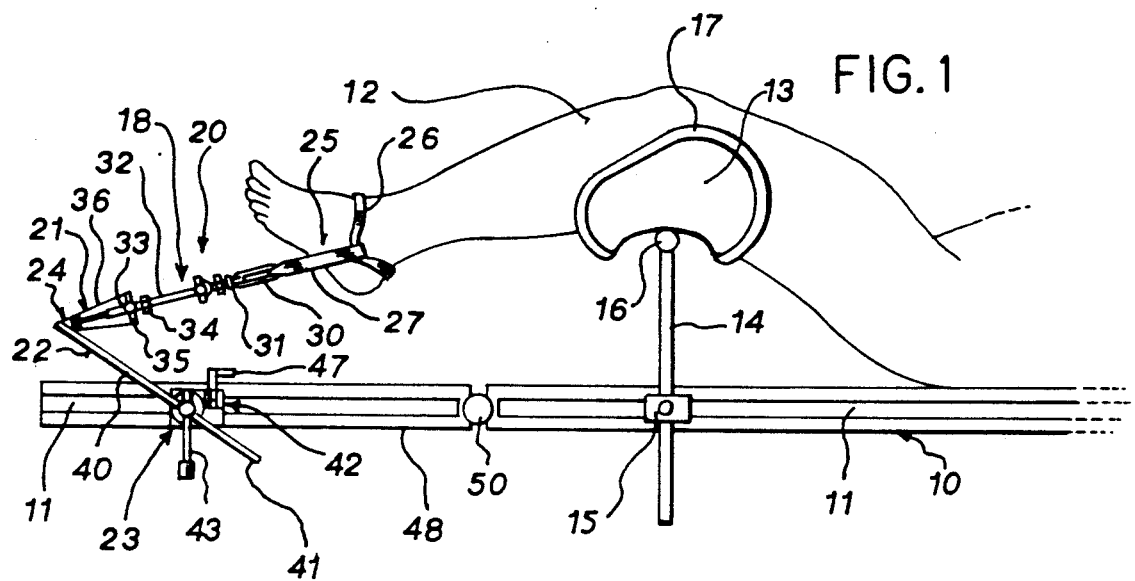
FIG. 1 is a side elevation showing the apparatus of the present invention attached to a patient with the leg in the slightly flexed position.

Referring initially to FIG. 1, a conventional operating table 10 includes a standard Clark rail 11 attached to one lateral edge of the table in a well known manner. The patient is positioned supine on the operating table 10 with the leg 12 of the patient supported at the back of the knee vertically above the table. The leg is only slightly flexed (nearly horizontal). Leg support is provided by a conventional gynecological or urological leg holder 13 attached in a known manner to the Clark rail 11. The leg holder 13 includes a support arm 14 adjustably attached to the Clark rail 11 by a clamp 15 which allows the assembly to be slid along the rail, pivoted in a horizontal plane, and moved vertically up or down. The upper end of the support arm 14 is connected to the leg holder 13 with a pivot mechanism 16 that allows the holder to be adjustably pivoted in either a horizontal or a vertical plane. The leg holder 13 can easily be adjusted in three planes of rotation and its height readily varied as will be described hereinafter. The leg is generously padded with a heavy foam rubber padding 17 to provide as much cushioning as is practicable, thereby minimizing as much as possible pressure on the posterior thigh and leg, primarily in the popliteal area.

The distraction apparatus of the present invention includes an axially adjustable distractor 18 attached by a first end 20 to the foot of the patient and by a second end 21 to the operating table, via a lever arm 22 having one end 23 pivotally attached to the Clark rail and the other end 24 connected to the second end 21 of the distractor 18.

Attachment of the distractor 18 to the foot of the patient is provided by a foot strap 25 including an adjustable VELCRO fastener band 26 placed around the ankle above the heel and instep and a connecting strap 27, including looped ends 28 on either side of the foot through which the VELCRO fastener band 26 is threaded. The doubled connecting strap 27 is threaded through a connector loop 30 attached to the first end 20 of the distractor by a swivel joint 31.

Figure 6:
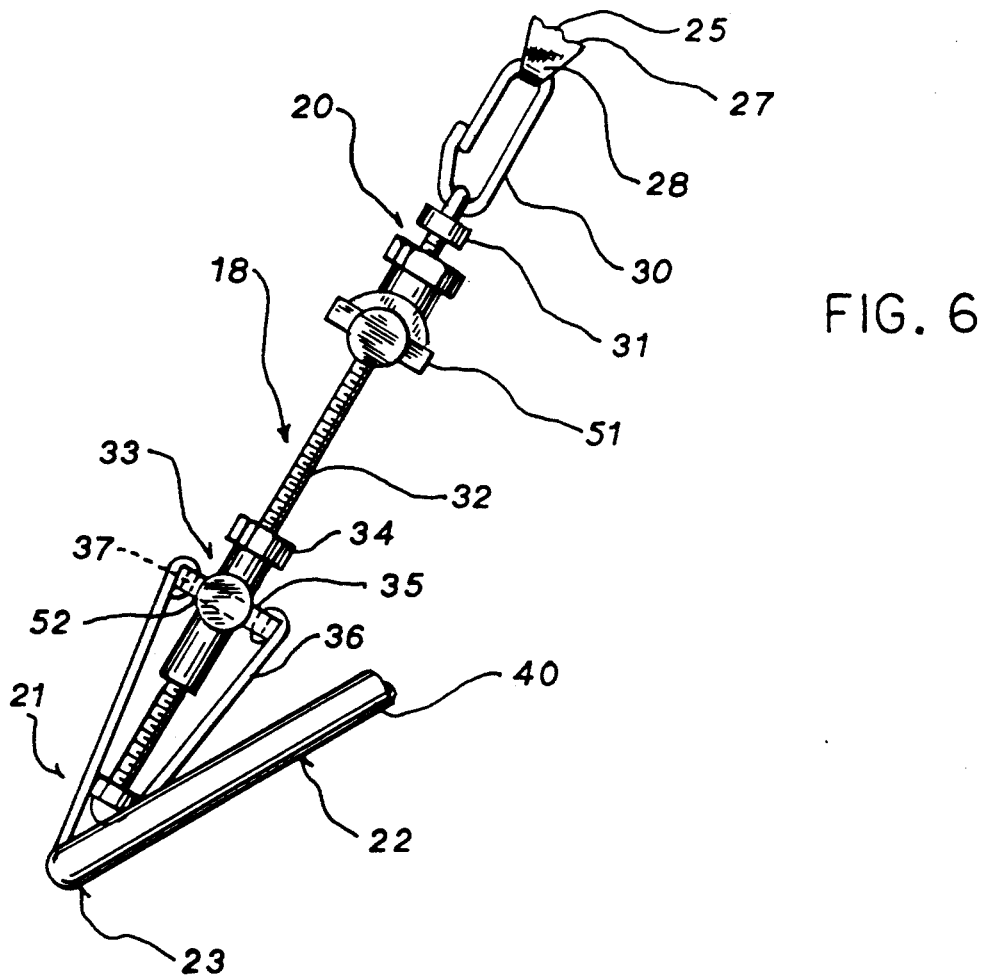
FIG. 6 is an enlarged side view of a portion of FIG. 4.
Figure 5:
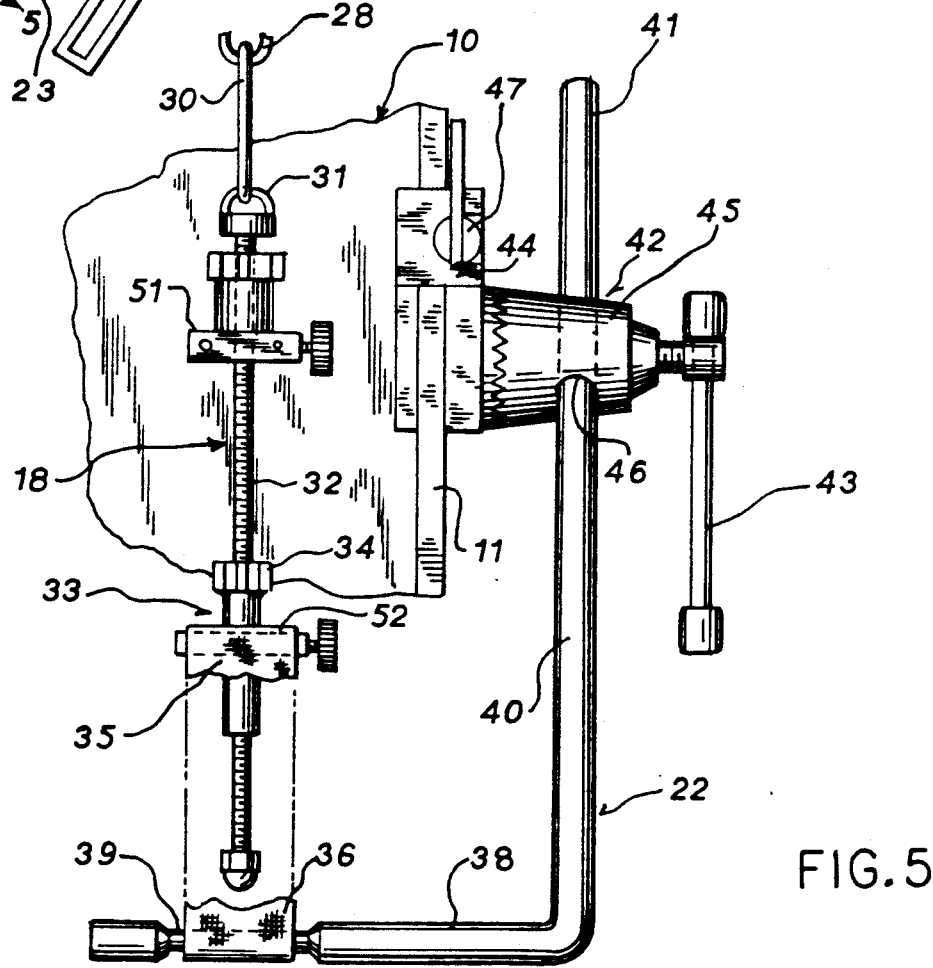
FIG. 5 is an end elevation of the apparatus and patient taken on line 5—5 of FIG. 4 and in a plane generally parallel to the hinged end of the table.

Referring also to FIGS. 5 and 6, the main body of the distractor 10 comprises a long threaded bolt 32 to which the swivel joint 31 is attached. A length adjustment mechanism 33 is attached to the second end 21 of the threaded bolt 32. The adjustment mechanism includes a manually operable, threaded adjustment nut and an attached mount 35 for an attachment strap 36. The mount 35 is connected to the adjustment nut 34 with a swivel connection so that the adjustment nut 34 can be rotated on the threaded bolt 32 to change the position of the adjustment mechanism therealong without rotating the mount 35 or attachment strap 36. The attachment strap 36 may comprise a piece of conventional nylon webbing or the like extending through slots 37 on opposite sides of the mount 35 and looped around one leg 38 of the L-shaped lever arm 22, as best seen in FIG. 5. The end of leg 38 includes a reduced diameter section 39 within which the strap 36 is placed to prevent it from slipping off.

The other leg 40 of the lever arm 22 has its free end 41 attached to the Clark rail 11 for adjustable positioning rotationally about its free end 41 and axially along the leg 40. Attachment of the leg 40 to the Clark rail 11 is provided by an adjustable clamp 42. The clamp includes a clamp body 44 mounted for slidable movement along the Clark rail 11 and a clamp head 45 rotatably attached to the clamp body and movable into clamping engagement therewith by rotation of an operating arm 43. The clamp body includes a set screw 47 for fixing the position of the clamp along the Clark rail. The clamp head 45 includes a diametral through bore 46 for receiving the leg 40 of the lever arm 22, and the clamp head is configured internally to simultaneously clamp the leg 40 in the bore 46 and the clamp head to the clamp body 44 by rotation of the operating arm 43. Similarly, rotation of the operating arm in the opposite direction simultaneously unclamps the clamp head 45 from the body so the head and lever arm may be rotated with respect thereto and the leg 40 can be positioned axially in the through bore 46.

Arthroscopic procedures utilizing non-invasive distraction techniques are preferably commenced utilizing the distraction position shown in FIG. 1. The support arm 14 for the leg holder 3 is positioned in a mid-height position and fixed with the clamp 15. With the patient in a supine position, the leg is placed in the leg holder 13 with the knee slightly flexed to about 20°. This initial position of near extension reduces the pressure on the posterior thigh and leg, primarily the popliteal area. The VELCRO fastener band 26 is placed around the foot and is attached to the end of the distractor 18 by the connecting strap 27. The other end of the distractor is attached to the horizontal leg 38 of the L-shaped lever arm 22 by the attachment strap 36, and the other leg 40 of the lever arm is initially positioned loosely in the through bore 46 in the clamp head 45. The clamp body 44 is positioned in an appropriate position on the Clark rail 11 and clamped thereto with the set screw 47. The lever arm 22 is then manually rotated (e.g. by the surgeon's assistant) around the end 41 held in the clamp 42 in a counterclockwise direction as viewed in FIG. 1. The position of clamp 42 on the Clark rail or the position along the leg 40 of the lever arm 22 may be adjusted as necessary to place the axis of the distractor 18 generally axial alignment with the lower leg of the patient. Continued rotation of the lever arm 22 in the clockwise direction will impose a tensile load on the ankle joint and provide an initial level of joint distraction. The initial level of distraction need only be very slight and just enough to hold the patient's leg and the apparatus firmly in position. The operating arm 43 of the clamp 42 is then turned to clamp the lever arm leg 40 in the through bore 46 to simultaneously establish its angular position with respect to the operating table and its axial position along the length of the leg.

With the leg and distractor held firmly in its initial position, the final desired level of joint distraction may be reached by turning the adjustment nut 34 on the adjustment mechanism 33 to change its position along the threaded bolt 32, to increase or decrease the tensile force applied to the foot strap 25 and thus the level of distraction force. The level of distraction is generally judged by the surgeon based on his preliminary examination of the patient and considering such factors as the nature of the pathology, the age of the patient, the relative degree of ligament laxity, and other indications. After the arthroscope has been inserted into the joint, the need for increased (or even decreased) distraction may be indicated. Any desired adjustment can be easily made by turning the adjustment nut 34.

Figure 2:
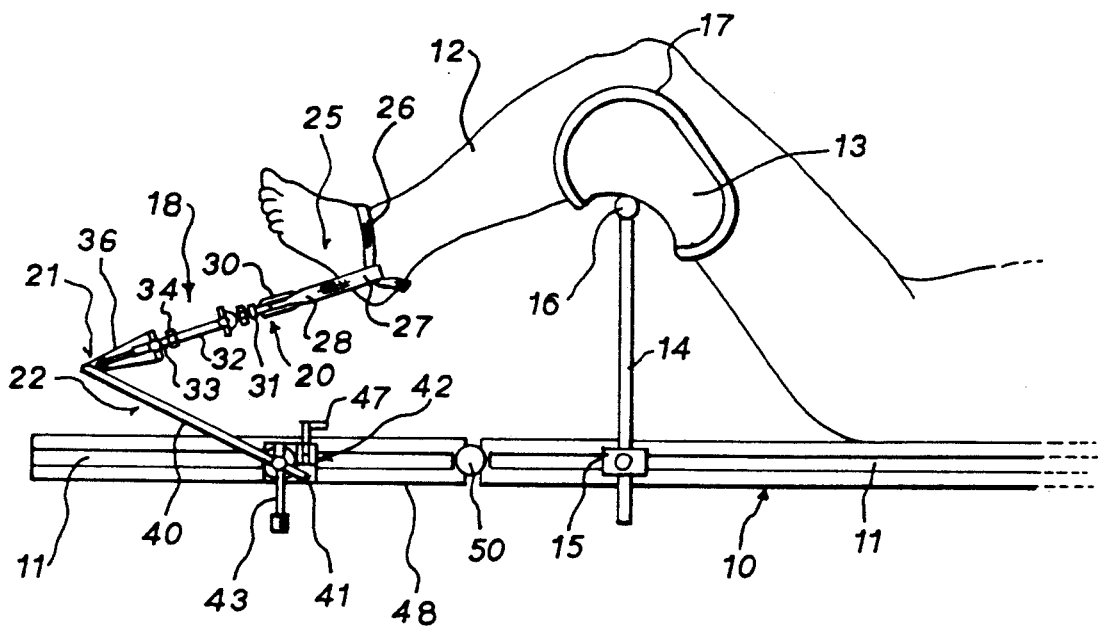
FIG. 2 is a side elevation similar to FIG. i showing the leg of the patient in a more acutely flexed position.

If additional distraction is needed beyond a level which can be adequately supported by the patient's knee only slightly flexed (FIG. 1), it may be necessary to more acutely flex the knee to a position shown, for example, in FIG. 2. The FIG. 2 angle of the lower leg may also position the posterior of the ankle joint in a more desirable position for the surgeon requiring entry through the posterior portals. The adjustment from the FIG. 1 to the FIG. 2 position is easily effected by raising the leg holder 13 to a slightly higher position and sliding the clamp 42 along the Clark rail 11 toward the leg holder. These adjustments may be made simply and with little loss of time and without affecting the sterile draping. Also, no other repositioning of the distraction apparatus may be needed, although as shown in FIG. 2, the leg 40 of the lever arm 22 may be lengthened somewhat with respect to the position of the free end 41 of the leg in the clamp 42.

In either of the FIG. 1 or FIG. 2 positions, it will be appreciated that the vertical position of the ankle above the operating table 10 can be varied considerably and as desired by varying the position of the leg 40 of the lever arm in the adjustable clamp 42. Furthermore, if necessary, the leg could be flexed even more acutely than shown in the FIG. 2 position with similar adjustments to the leg holder and distractor as previously described. However, in the more acutely flexed positions, the pressure which can be applied to the popliteal area is potentially greater and circulation must be monitored.

Figure 3:
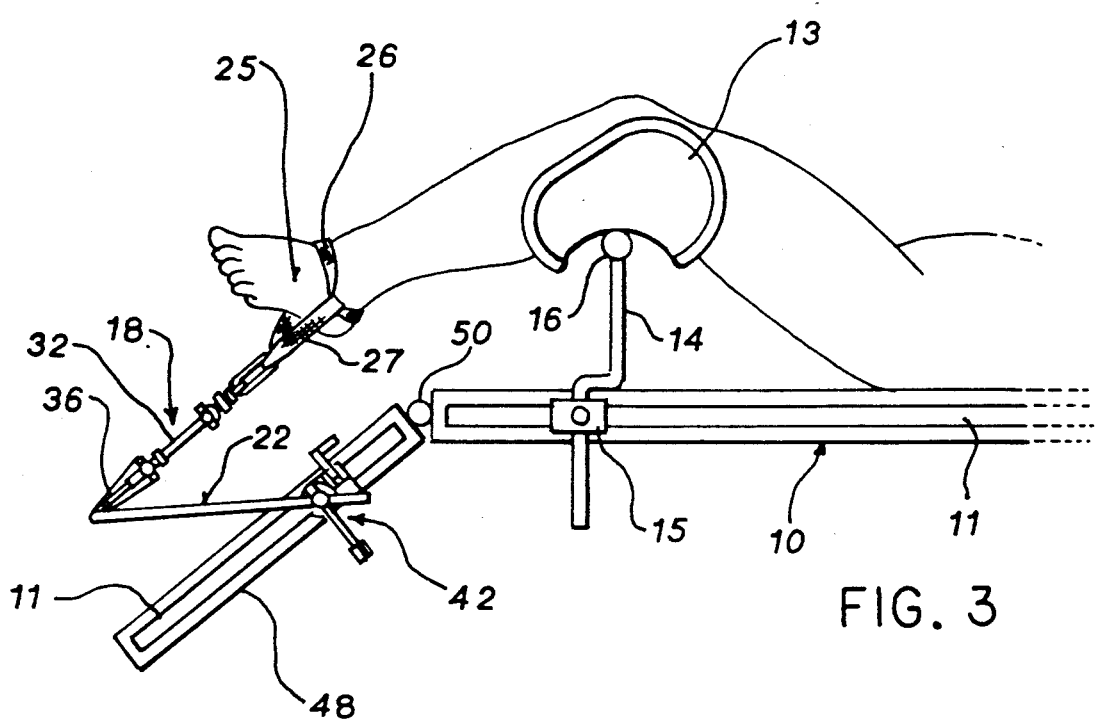
FIG. 3 is a side elevation showing the apparatus of the present invention utilized with the hinged end of the operating table tilted downwardly.
Figure 4:
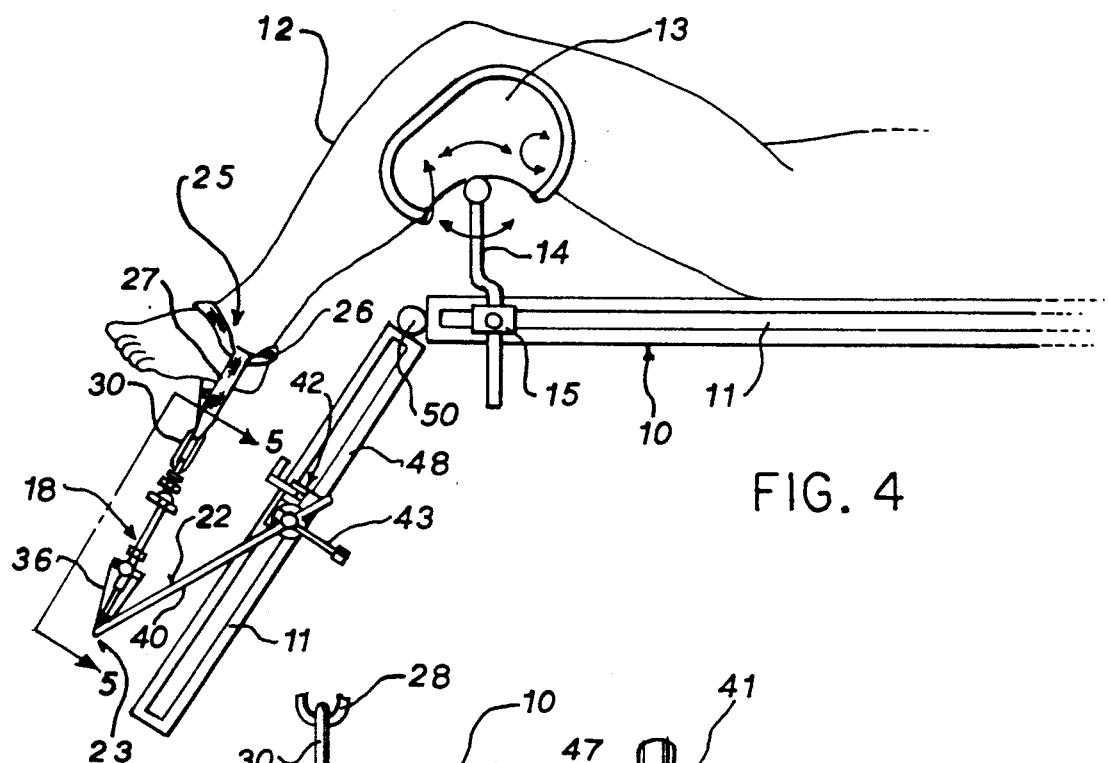
FIG. 4 is a side elevation similar to FIG. 3 showing the hinged end of the table tilted further downwardly.

To facilitate certain procedures or to accommodate the personal preference of the surgeon, the apparatus and method of the present invention allows further significant adjustments in the height and relative position of the ankle joint in a manner utilizing simple adjustment of the type previously described, with little loss of time, and without affecting the sterile draping. By additionally utilizing a table end 48 which can be pivoted or tilted downwardly about a laterally disposed hinge 50 and locked in a tilted position, the lower leg may be positioned nearly vertical or even below the level of the operating table 10, if desired. The hinge 50 is positioned between the adjustable clamp 42 for the lever arm and the clamp 15 for the leg holder support arm 14. The leg holder clamp 15 may be adjusted to position the leg holder close to the hinge 50 to accommodate the downwardly depending positions of the leg as shown in FIGS. 3 and 4. The FIG. 3 position may be suitable for most diagnostic work and some surgery. In this position, the ankle may be placed closer vertically to the horizontal top of the operating table, but because of the downwardly dependent table end 48, the table does not provide as significant an obstruction to surgeon procedures and access to the entire ankle joint is relatively uninhibited.

If posterior lateral entry is required or if a lower position of the ankle is more convenient to the surgeon, the table end 48, may be tilted downwardly to an even greater acute angle with respect to the horizontal table top and locked in the FIG. 4 position. This position may require the leg holder to be positioned closer to the hinge by repositioning the leg holder clamp 15. This, in turn, may also necessitate repositioning the adjustable clamp 42 on the table end 48 to move it closer to the distal end thereof.

Should invasive distraction techniques, such as those described in my prior U.S. Pat. No. 5,063,918, become necessary during procedures performed in any of the positions of FIGS. 1–4, conversion to such invasive techniques can be made quickly and without reprepping or redraping as indicated in that patent. As may best be seen in FIGS. 5 and 6, the distractor 18 includes an adjustable head 51 for holding the pins used in invasive distraction techniques and, similarly, the mount 35 on the adjustment mechanism 33 at the other end of the distractor includes a similar head 52 for the other pins used in an invasive procedure, all as described in the above identified patent. Thus, in converting from the non-invasive techniques described herein, to an invasive technique, the same distractor 18 can be utilized. This provides both a convenience to the surgeon and a significant cost saving.

Various modes of carrying out the present invention are contemplated as being within the scope of the following claims particularly pointing out and distinctly claiming the subject matter which is regarded as the invention.

I claim:

1. A non-invasive distraction system for ankle joint arthroscopy comprising in combination:
   an operating table for supporting a patient in a generally supine position;

a leg holder adapted to adjustably support the leg of the patient posteriorly of the knee joint to maintain the leg in a selected position between slightly flexed and acutely flexed, said leg holder attached directly to one edge of the operating table below the knee and including means of adjusting the height of the knee joint above the table and for pivoting the leg holder in each of three mutually perpendicular planes;

distraction means including an elongate body having an axially adjustable length and having first and second ends, said first end adapted to be attached to the foot of the patient;

a manually operable lever arm having one end attached to the table and an opposite end attached to the second end of said elongate body;

an adjustable clamp attached to one edge of said table, said clamp including first clamping means for selective positioning of said clamp along said table edge and second clamping means for attaching the opposite end of said lever arm to the table to permit the lever to be rotated manually about said one end in a generally vertical plane and clamped in a selected position imposing a tensile load on said elongate body to provide an initial level of ankle joint distraction; and, means for adjusting the length of said elongate body to vary said initial level of ankle joint distraction.

2. The system as set forth in claim 1 including:

a hinged joint in said operating table, said joint extending across the table normal to said table edge and positioned between the leg holder height adjusting means and said adjustable clamp to provide a hinged table end supporting said clamp; and, means for tilting said table end downwardly to a variable selected acute angled position with respect to the plane of table and for locking said table end in said angled position;

whereby said adjustable clamp, said lever arm and said distraction means are positionable below the top of said table.

3. A non-invasive distraction system for ankle joint arthroscopy comprising in combination:

an operating table for supporting a patient in a generally supine position;

a leg holder adapted to adjustably support the leg of the patient posteriorly of the knee joint to maintain the leg in a selected position between slightly flexed and acutely flexed, said leg holder attached directly to the operating table below the knee and including means for adjusting the height to the knee joint above the table;

distraction means including an elongate body having an axially adjustable length and having first and second ends, said first end adapted to be attached to the foot of the patient;

an adjustable clamp attached to one edge of said table, said clamp including clamping means for selective positioning of said clamp along said table edge and means for attaching the second end of said elongate body to the table to permit said elongate body to be positioned spaced from the bottom of the foot of the patient with the axis of said elongate body disposed generally axially of the lower leg to establish an initial foot support position and to provide an initial level of ankle joint distraction;

means for adjusting the length of said elongate body to vary said initial level of ankle joint distraction; and means for hinging the operating table on a line transverse to sad table edge between the leg holder height adjusting means and said adjustable clamp to define a hinged table end of supporting said clamp and said distraction means below the top of said table.

4. The system as set forth in claim 3 wherein the means for attaching the second end of said elongate body to the table comprises:

a manually operable lever arm having one end attached to said adjustable clamp to permit the lever to be rotated about said one end in a generally vertical plane and to be clamped in a selected position to provide said initial level of ankle joint distraction.

5. A method for providing non-invasive ankle joint distraction to facilitate ankle arthroscopy, said method comprising the steps of:

(1) supporting the patient on a table in a generally supine position;

(2) adjustably positioning a leg of the patient to selectively maintain the leg between slightly flexed and acutely flexed positions by supporting the leg with a support beneath the knee joint, said support adjustably attached to one lateral edge of the table for moving the support vertically and pivoting the support in any of three planes of rotation with respect to the table;

(3) pivotally attaching one end of a lever arm to one edge of the table;

(4) attaching a first end of an axially adjustable distraction device to the foot of the patient, and attaching a second end of the distraction device to the other end of the lever;

(5) manually rotating said one end of the lever arm about the pivotal connection of said other end in a generally vertical plane to impose a tensile load on said distraction device to provide an initial level of ankle joint distraction;

(6) clamping said other end of the lever arm to maintain said initial lever of ankle joint distraction; and, (7) adjusting the length of said distraction device to vary said initial level of ankle joint distraction.

* * * * *